US012642987B2

(12) United States Patent
Dijkstra et al.

(10) Patent No.: US 12,642,987 B2
(45) Date of Patent: Jun. 2, 2026

(54) CHARGING DEVICE FOR A PHOTOTHERAPY PATCH

(71) Applicant: Shenzhen Kaiyan Medical Equipment Co., Ltd, Shenzhen (CN)

(72) Inventors: Alain Dijkstra, Amstelveen (NL); Li Xiang, Shenzhen (CN); Chen Shoufeng, Shenzhen (CN); Wu Guoqiu, Shenzhen (CN)

(73) Assignee: Shenzhen Kaiyan Medical Equipment Co., Ltd (CN)

( * ) Notice: Subject to any disclaimer, the term of this patent is extended or adjusted under 35 U.S.C. 154(b) by 0 days.

(21) Appl. No.: 19/050,432

(22) Filed: Feb. 11, 2025

(65) Prior Publication Data

US 2026/0145002 A1     May 28, 2026

(30) Foreign Application Priority Data

Nov. 27, 2024    (CN) .......................... 202411711612.1

(51) Int. Cl.
 *A61N 5/06* (2006.01)
 *B65H 35/00* (2006.01)
 *H02J 7/70* (2026.01)

(52) U.S. Cl.
 CPC ......... *A61N 5/062* (2013.01); *B65H 35/0013* (2013.01); *H02J 7/731* (2026.01); *A61N 2005/0645* (2013.01); *A61N 2005/0651* (2013.01); *B65H 2701/1722* (2013.01)

(58) Field of Classification Search
 CPC ............ A61N 5/062; A61N 2005/0645; A61N 2005/0651; B65H 35/0013; B65H 2701/1722; H02J 7/0044

USPC ...................................................... 607/90, 91
See application file for complete search history.

(56) References Cited

U.S. PATENT DOCUMENTS

2006/0167532 A1* 7/2006 Parker .................. A61N 5/0616
                                                    607/88
2012/0316623 A1* 12/2012 Li ......................... A61N 5/0613
                                                    607/90
2016/0056653 A1* 2/2016 Tapper ................. A61N 5/0616
                                                    607/91
2021/0383966 A1* 12/2021 Ren ........................ H01F 27/255
2021/0393975 A1* 12/2021 Eltorai ............. A61F 13/00063
2025/0177774 A1* 6/2025 Macgilp ................ A61N 5/062

* cited by examiner

*Primary Examiner* — Ahmed M Farah
(74) *Attorney, Agent, or Firm* — Vani Moodley, Esq.

(57) ABSTRACT

The present invention relates to a charging device for a phototherapy patch. The charging device includes a housing that accommodates a charging unit to supply electrical power to at least one phototherapy patch. The charging unit is arranged within the housing and is configured to connect with the phototherapy patch during charging. The charging device includes a cavity circumferentially arranged around the charging unit to store adhesive tape. The cavity integrated within the charging unit allows the adhesive tape to be conveniently stored and accessed to secure the phototherapy patch to the user's skin. The charging device ensures efficient charging of the phototherapy patches while simultaneously providing a solution for storing adhesive materials which reduces contamination, misplacement, and handling issues associated with separately packed consumables.

8 Claims, 9 Drawing Sheets

CHARGING DEVICE FOR A PHOTOTHERAPY PATCH

TECHNICAL FIELD

The present invention relates to a phototherapy device. More specifically, the present invention relates to a charging device for a phototherapy patch.

BACKGROUND

Phototherapy is a non-invasive treatment that uses specific wavelengths of light to treat various skin conditions. The phototherapy relies on devices such as phototherapy patches, which are designed to deliver light directly to the skin for localized treatment. Generally, phototherapy patches are provided to target specific areas on the skin and are not feasible to hold on that period like the other phototherapy devices such as masks, goggles, or head caps.

Traditionally, materials like silicone layers or plastic shells have been employed as the primary light-emitting surfaces of phototherapy patches due to their durability, biocompatibility, and efficiency in light emission. However, these materials present difficulty in adhering to the skin surface, especially in dynamic environments or during prolonged use. This shortcoming often leads to detachment, reducing the efficacy of the treatment and causing inconvenience to users. Presently, the phototherapy patches are attached to the skin using adhesive tapes or stickers.

The adhesive tape material complements the phototherapy patch by securely attaching the silicone or plastic light-emitting layer to the skin. The adhesive is provided to enhance stability during use, even when the user moves or sweats. However, the consumable nature of these stickers introduces new challenges. The adhesive tapes are packed separately, making them vulnerable to contamination, misplacement, or omission during storage and handling. These factors can compromise the phototherapy patch's overall usability, hygiene, and therapeutic outcomes.

Therefore, there is a need for a charging device for a phototherapy patch to overcome a few or all drawbacks of the existing technologies.

STATEMENT OF THE INVENTION

An object of the present invention is to provide a charging device for a phototherapy patch.

Another object of the present invention is to provide a charging device for a phototherapy patch that is easy to carry and store, without compromising functionality or efficiency.

Yet another object of the present invention is to provide a charging device for a phototherapy patch that minimizes the risk of contamination, misplacement, or omission of consumables like adhesive tapes, improving ease of use for the user.

Another object of the present invention is to provide a charging device for a phototherapy patch that offers portability and ease of storage while maintaining functionality.

According to the present invention, a charging device for a phototherapy patch is provided. The charging device may include a housing, a charging unit and a cavity configured circumferentially around the charging unit.

The housing may include a base and a cover detachably attached to the base to refill an adhesive tape in the cavity. The base may include an inner wall and an outer wall. The inner wall and the outer wall may configure the cavity therebetween. The cavity may be enclosed using the cover attachable to the base to store an adhesive tape therein. Further, the inner wall of the base may form a central cavity at a central portion of the housing to accommodate the charging unit. The charging unit is enclosed in the central cavity using a central cover.

Furthermore, the cover may include an internal wall and an external wall adapted to align correspondingly over the inner wall and the outer wall of the base to enclose the cavity to store the adhesive tape therein.

The charging unit may be arranged in the housing and may be adapted to connect with at least one phototherapy patch for charging. Further, the cavity may be configured circumferentially around the charging unit to store an adhesive tape. In an aspect, the cavity is an annular cavity arranged around the charging unit. The annular cavity may be adapted to store and dispense a roll of adhesive tape. Additionally, the outer wall of the base and the external wall of the base may include an outwardly extending portion configuring an outlet port to dispense the adhesive tape therefrom.

In an aspect, the cover is attachable to the base through a locking mechanism. The locking mechanism may include a first locking element and a second locking element. The first locking element may be arranged on the base and the second locking element may be arranged on the cover which engageable with the corresponding first locking element.

In alternative aspect, a phototherapy unit for phototherapy treatment is provided. The phototherapy unit includes at least one phototherapy patch, and a charging device.

The charging device may include a housing adapted to receive at least one phototherapy patch, a charging unit arranged in the housing, and a cavity arranged circumferentially around the charging unit for storing adhesive tape. The charging unit may be adapted to connect with at least one phototherapy patch.

The housing may include at least one receiving portion adapted to receive and attach at least one phototherapy patch to the housing. Further, the housing may include a recessed portion, depressed on the housing forming a space to insert fingers of the user around the phototherapy patch. The recessed portion may facilitate the user to hold and detach the phototherapy patch from the housing.

In an aspect, the housing may include a first receiving portion and a second receiving portion to receive a first phototherapy patch and a second phototherapy patch respectively. Further, at least one receiving portion may be arranged on the central cover to receive at least one phototherapy patch.

In the present aspect, the housing may include a base and a cover detachably attached to the base. The base may include an inner wall and an outer wall. The inner wall of the base may form a central cavity at a central portion of the housing to accommodate the charging unit. Additionally, the charging unit may be enclosed using the central cover. The central cover may include at least one receiving portion to receive at least one phototherapy patch.

In the present aspect, the charging unit may include a circuit board, a battery connected to the circuit board, and a charging port arranged on the circuit board. The charging port may be adapted to receive an external power to charge the battery. The charging unit may be adapted to establish an electrical connection between the charging unit and the phototherapy patch. Specifically, the charging unit includes a charging connector engageable with a charge receiving connector of the phototherapy patch to receive an electrical charge. The charging connector may include a first connector and a second connector, exposed from at least one receiving portion. The charge receiving connector of the phototherapy patch may include a third connector and a fourth connector adapted to connect with the first connector and the second connector respectively.

Additionally, at least one receiving portion may include an aligning slot, and at least one phototherapy patch may include an aligning protrusion to receive at least one phototherapy patch in at least one receiving portion in such a way that the first connector aligns with the third connector and the second connector aligns with the fourth connector.

In the present aspect, the phototherapy patch may include a patch housing adapted to accommodate a patch battery and a patch circuit board. The patch circuit board may include a light source for phototherapy treatment and a charge receiving connector to receive electric charge from the charging unit when attached.

Further, the patch housing may include a transparent plate to enclose the patch battery, and the patch circuit board within the patch housing. The transparent plate may allow light to emit from the light source on the skin of the user.

BRIEF DESCRIPTION OF DRAWINGS

Other features and advantages of the invention will become apparent when reading the detailed description given below, purely by way of example and in a non-limitative manner, referring to the following figures:

FIG. 6a shows a perspective view of a phototherapy unit along with the charging device in accordance with a second embodiment of the present invention;

FIG. 6b shows an exploded view of the phototherapy unit illustrated in FIG. 6a;

FIG. 8 shows a perspective view of the charging device along with a central cavity in accordance with the embodiment shown in FIG. 6a;

FIG. 9 shows a perspective view of a phototherapy patch in accordance with the second embodiment shown in FIG. 6a.

DETAILED DESCRIPTION

An embodiment of this invention, illustrating its features, will now be described in detail. The words "comprising," "having," "containing," and "including," and other forms thereof, are intended to be equivalent in meaning and be open-ended in that an item or items following any one of these words is not meant to be an exhaustive listing of such item or items, or meant to be limited to only the listed item or items.

The present invention provides a charging device for a phototherapy patch. The charging device is provided to integrate a storage space for the adhesive tapes to avoid contamination, misplacement, or omission during storage and handling.

The terms "first," "second," and the like, herein do not denote any order, quantity, or importance, but rather are used to distinguish one element from another, and the terms "a" and "an" herein do not denote a limitation of quantity but rather denote the presence of at least one of the referenced item.

The disclosed embodiments are merely exemplary of the invention, which may be embodied in various forms.

Figure 1:
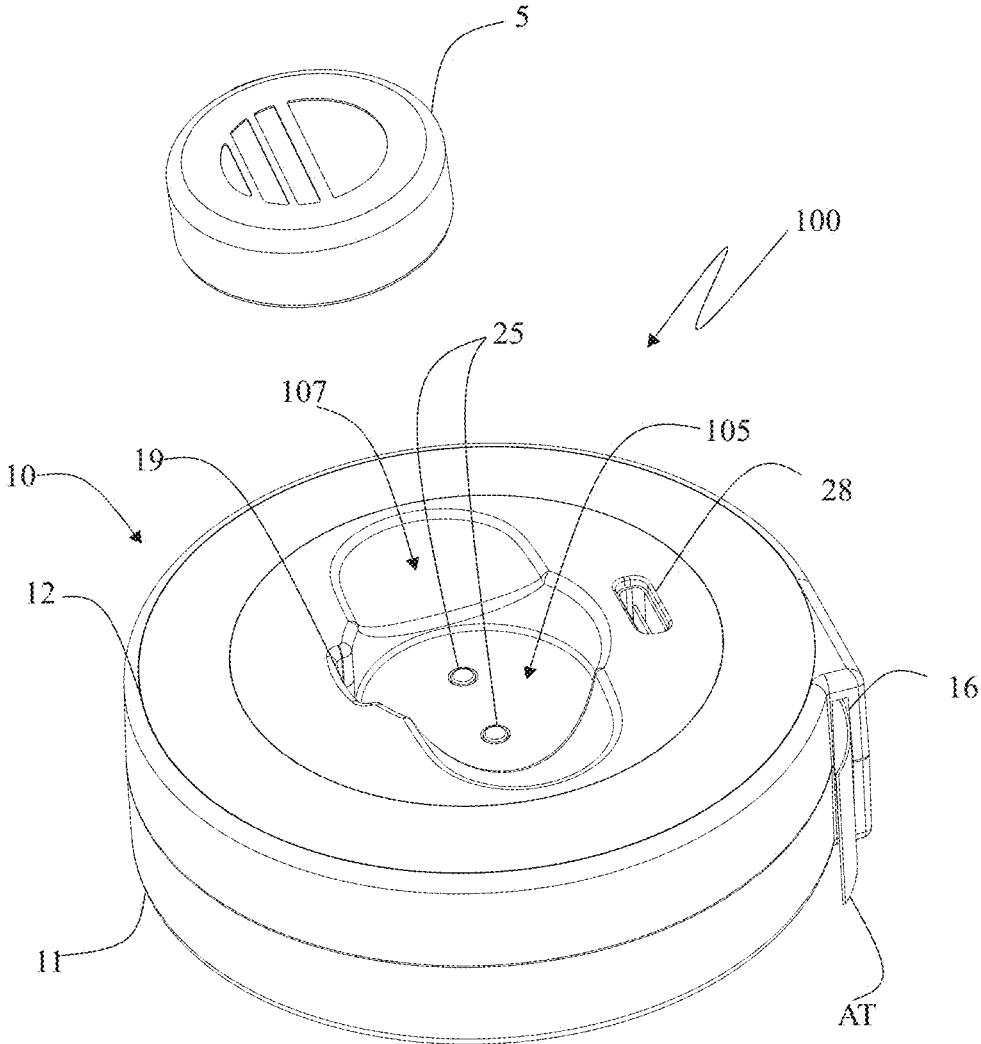
FIG. 1 shows a perspective view of a charging device in accordance with the present invention.
Figure 2:
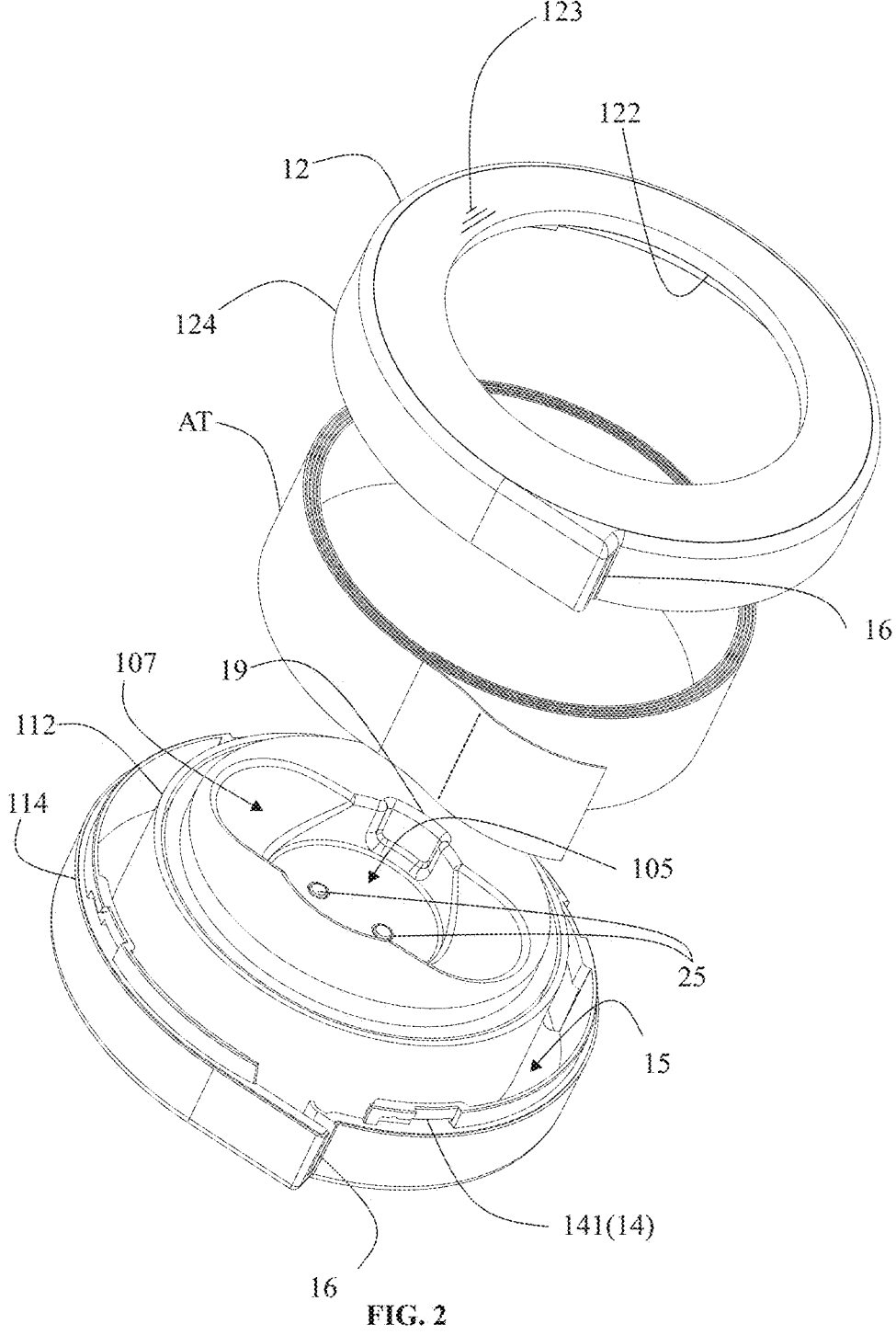
FIG. 2 shows an exploded view of the charging device along with a roll of adhesive patch.

Referring now to FIGS. 1, and 2, a charging device 100 for a phototherapy patch 5 in accordance with the present invention is illustrated. The charging device 100 includes a housing 10, a charging unit 20 arranged in the housing 10, and a cavity 15 configured circumferentially around charging unit 20 to store adhesive tape AT.

The housing 10 includes a base 11 and a cover 12 detachably attached to the base 11. Specifically, the base 11 includes an inner wall 112 and an outer wall 114 to configure the cavity 15 therebetween to store adhesive tape AT.

In the present preferred embodiment, the cavity 15 is an annular cavity configured around the charging unit 20. The inner wall 112 and the outer wall 114 are circular-shaped walls, spaced apart at a radial distance. The outer wall 114 has a bigger diameter than the inner wall 112 to configure the annular cavity therein. The cavity 15 is adapted to store and dispense a roll of adhesive tape AT. It is obvious for a person skilled in the art to configure the cavity 15 circumferentially around the charging unit 20 in any other shape such as triangular, rectangular, pentagonal, hexagonal, or polygonal.

In an alternative embodiment, the inner wall 112 and the outer wall 114 may have different shapes such as the inner wall 112 having a circular shape and the outer wall 114 having a rectangular shape.

Figure 3:
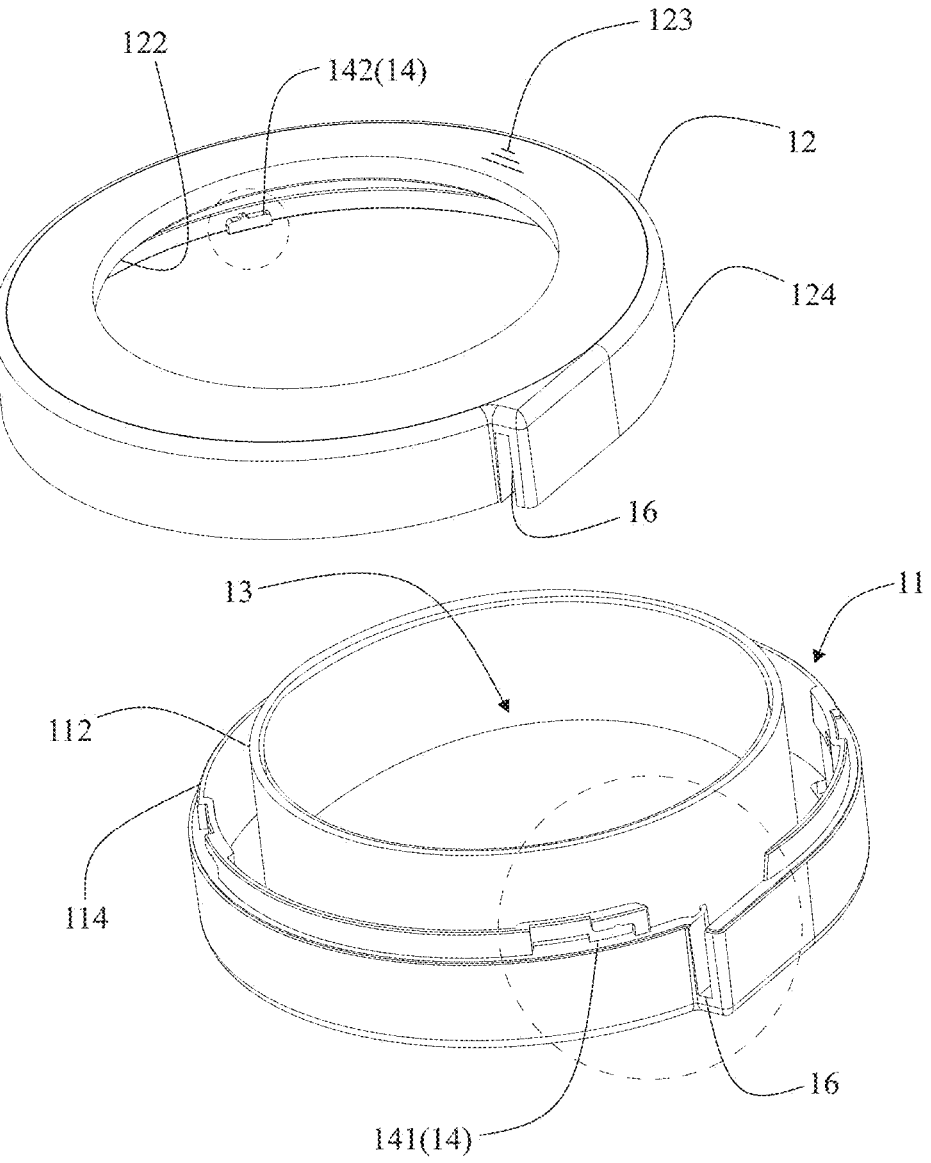
FIG. 3 shows a perspective view of a base and a cover of the charging in accordance with the present invention.

Referring now to FIG. 3, the cover 12 is provided to cover 12 the cavity 15 in the axial direction. The cover 12 is detachably connected to the base 11 to enable the refilling of the adhesive tape AT in the cavity 15. Specifically, the cover 12 includes an internal wall 122 and an external wall 124 adapted to align correspondingly over the inner wall 112 and the outer wall 114 of the base 11 to enclose the cavity 15 to store the adhesive tape AT therein securely. Specifically, the cover 12 includes a top wall 123 to separate the internal wall 122 and the external wall 124 spaced at a radial distance. In the present embodiment, the internal wall 122 and the external wall 124 have a circular shape. The external wall 124 has a larger diameter than the internal wall 122. In an alternative embodiment, the external wall 124 and the internal wall 122 may have different shapes such as the internal wall 122 having a circular shape and the external having a rectangular shape.

Specifically, the shape of the internal wall 122 and the external wall 124 of the cover 12 corresponds to the shape of the inner wall 112 and the outer wall 114 of the base 11.

The outer wall 114 of the base 11 and the external wall 124 of the base 11 include an outwardly extending portion configuring an outlet port 16 to dispense the roll of adhesive tape AT therefrom. The outlet port 16 is an opening to dispense the adhesive tape AT. Specifically, while refilling the roll of adhesive tape AT, the adhesive tape AT is pulled out of the outlet port 16 and is adapted to roll out according to the user's requirement avoiding misplacement or the contamination of the adhesive tape AT.

In alternative embodiments, the adhesive tape AT can be a drug patch, such as vitamin E gel patch, which can be stuck to the skin directly, and can also release drug ingredients to treat or maintain the skin when the adhesive tape AT is stuck on the skin to improve the treatment effect in cooperation with the phototherapy patch 5.

In another embodiment, the cavity 15 is adapted to store adhesive patches individually, rather than the roll of adhesive tape AT.

Figure 4A:
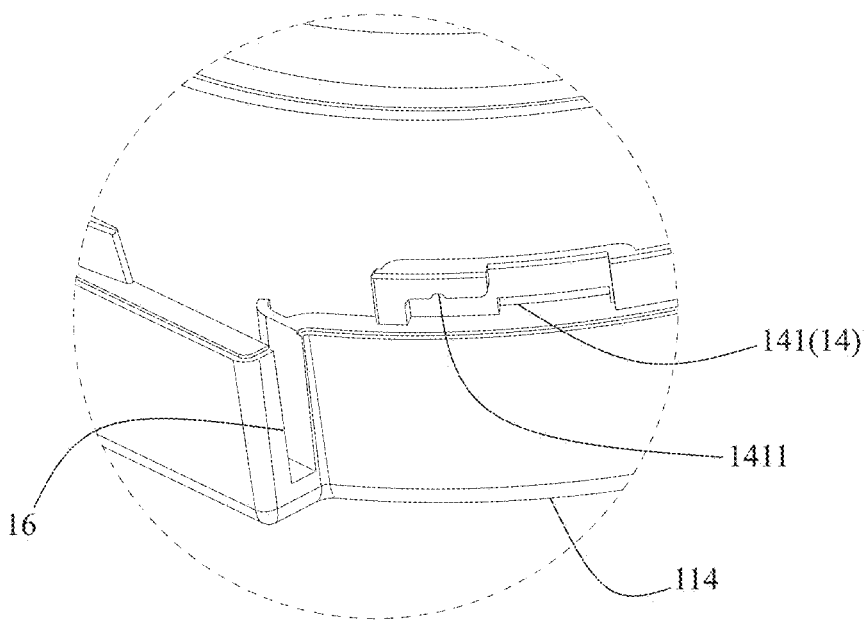
FIG. 4a shows an enlarged view of a first locking element of the base shown in FIG. 3.
Figure 4B:
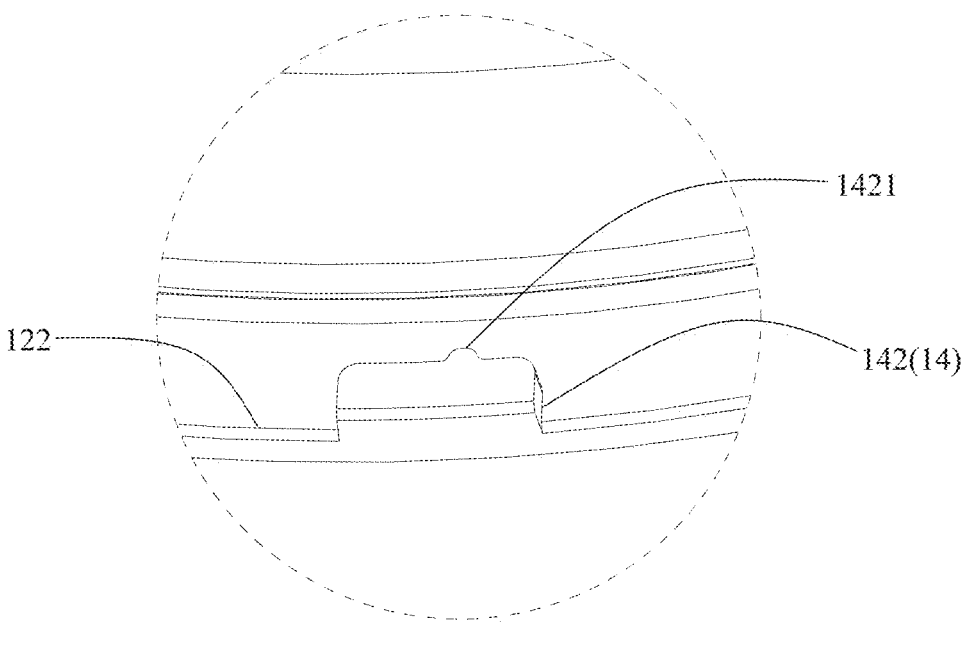
FIG. 4b shows an enlarged view of a second locking element of the cover shown in FIG. 3.

Referring now to FIGS. 3, 4a, and 4b, the cover 12 is detachably attachable to the base 11 through a locking mechanism 14. The locking mechanism 14 includes a first locking element 141 and a second locking element 142. Specifically, the first locking element 141 is arranged on the base 11 and the second locking element 142 is arranged on the cover 12. The second locking element 142 is engageable with the corresponding first locking element 141 of the base 11.

In the present embodiment, the first locking element 141 is a locking portion and the second locking element 142 is an engaging portion which is engageable with the locking portion. In an alternative embodiment not shown, the first locking element 141 is an engaging portion and the second locking element 142 is a locking portion which is engageable with the engaging portion. The first locking element 141 and the second locking element 142 facilitate the attachment of the base 11 and the cover 12. The first locking element 141 and the second locking element 142 engage or disengage from each other to provide attachment and detachment of the base 11 and cover 12 according to the user's requirement to refill the adhesive tape AT.

Figure 5:
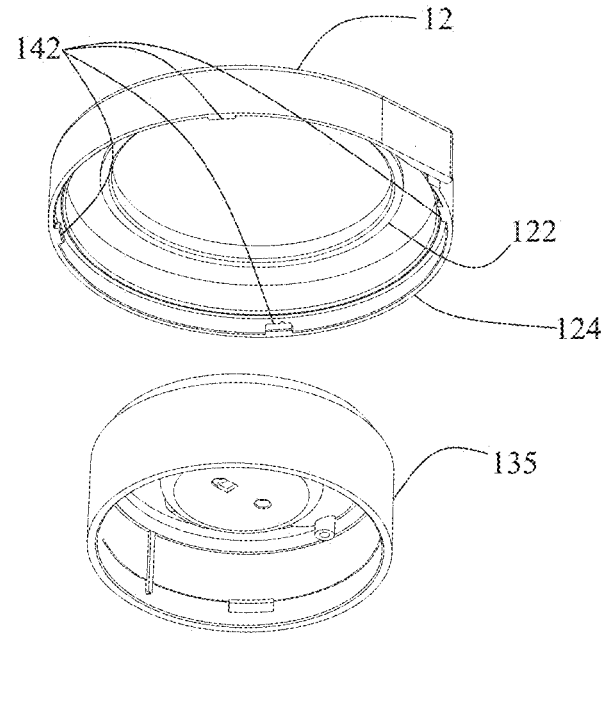
FIG. 5 shows an exploded view of the charging device in accordance with the present invention.
Figure 5:
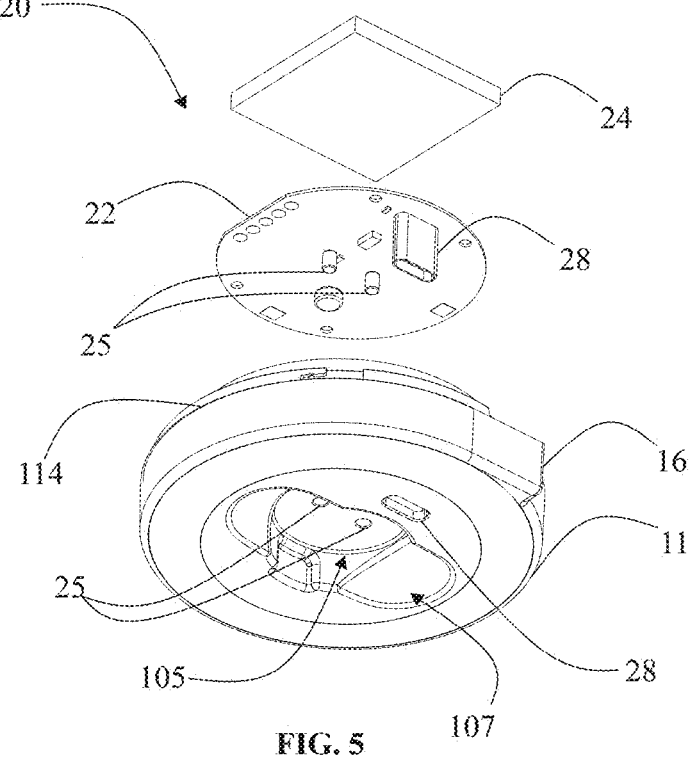

Further, the base 11 includes a plurality of first locking elements 141 as shown in FIG. 5, preferably arranged on the outer wall 114 of the base 11, and the cover 12 includes a plurality of second locking elements 142, preferably arranged on the external wall 124 of the cover 12 corresponding to the plurality of first locking elements 141. The plurality of first locking elements 141 and the plurality of second locking elements 142 provide stability to the base 11 and the cover 12 when attached.

Referring now to FIGS. 4a, and 4b, the first locking element 141 is having a L-shaped structure configured on the outer wall 114 of the base 11, facing outwardly away from the center of the base 11, and the second locking element 142 is configured on the external wall 124 of the cover 12, facing inwardly towards the center of the cover 12. The first locking element 141 and the second locking element 142 are arranged in such a way that when attached, an edge of the external wall 124 of the cover 12 contacts with an edge of the outer wall 114 of the base 11 to provide sealing.

Further, the first locking element 141 includes a positioning slot 1411 and the second locking element 142 includes a positioning protrusion 1421. The positioning protrusion 1421 is adapted to engage with the positioning slot 1411. Specifically, when the cover 12 is placed on the base 11, inserting the second locking element 142 in the L-shaped structure of the first locking element 141. The cover 12 is rotatable to engage the positioning protrusion 1421 with the corresponding positioning slot 1411 of the first locking element 141, thereby attaching the cover 12 with the base 11 and maintaining stability. The first locking element 141 and the second locking element 142 are aligned in such a way that the outlet port 16 is configured thereon.

In an alternative embodiment not shown, the first locking element 141 is a first magnetic member and the second locking element 142 is the second magnetic member. The first magnetic member and the second magnetic member are provided on the base 11 and the cover 12 respectively to facilitate magnetic attachment and detachment of the cover 12 and the base 11. Preferably, the first magnetic member is arranged on the edge of the outer wall 114 and/or the inner wall 112 of the base 11 The second magnetic member is arranged on the edge of the external wall 124 and/or the internal wall 122 of the cover 12 to attach the external wall 124 to the outer wall 114 and/or attach the internal wall 122 to the inner wall 112 magnetically.

Referring now to FIGS. 2, 3 and 5, the charging unit 20 is arranged in the housing 10 and is adapted to connect with at least one phototherapy patch 5. The housing 10 is adapted to receive at least one phototherapy patch 5 to charge the phototherapy patch 5. Specifically, the housing 10 includes a receiving portion 105 which is adapted to receive and hold at least one phototherapy patch 5 for charging. The charging unit 20 is arranged at a center of the housing 10 within a central cavity 13 and a charging connector 25 of the charging unit 20 is exposed from the receiving portion 105 to charge the phototherapy patch 5.

The receiving portion 105 is a depressed region on the housing 10 having a shape corresponding to the phototherapy patch 5 to allow the phototherapy patch 5 to fit completely flush within the housing 10. The charging unit 20 is configured to connect and supply an electric charge to the phototherapy patch 5 while the phototherapy patch 5 is not being used and is attached to the housing 10.

Further, the charging unit 20 includes a circuit board 22, and a battery 24 connected to the circuit board 22. The circuit board 22 is configured to expose the charging connector 25 from the receiving portion 105 to charge the phototherapy patch 5 attached to the receiving portion 105.

The charging device 100 integrates the cavity 15 to store and dispense the adhesive tape AT to provide a portable charging device that secures at least one phototherapy patch 5 while not being used. The phototherapy patch 5 is configured to receive the electrical charge from the charging unit 20. The housing 10 of the charging device 100 is adapted to receive any type of phototherapy patch 5 and provide the electric charge when attached to the housing 10, simultaneously, the charging device 100 is adapted to store the adhesive patch, allowing the user to conveniently use adhesive patches for attaching the phototherapy patch 5 to the skin.

Figures 6A, 6B:
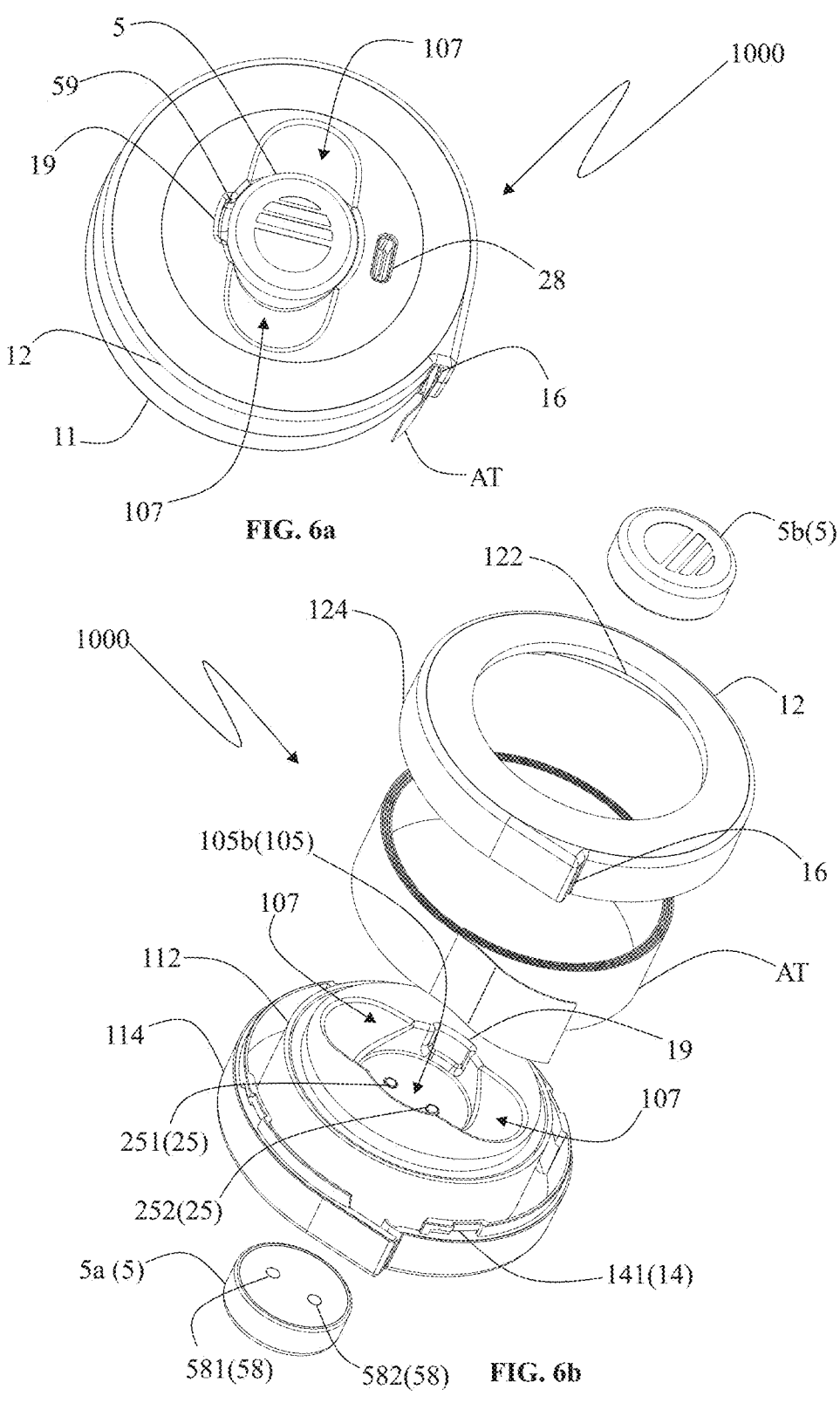

Referring now to FIGS. 6a-6b, in a second embodiment of the present invention, a phototherapy unit 1000 for phototherapy treatment is provided. The phototherapy unit 1000 includes at least one phototherapy patch 5, a housing 10 adapted to receive at least one phototherapy patch 5, a charging unit 20 arranged in the housing 10, and a cavity 15 arranged circumferentially around the charging unit 20 for storing adhesive tape AT.

The phototherapy patch 5 is adapted to provide phototherapy treatment on the skin of the user. In another embodiment, the phototherapy patch 5 is a microcurrent therapy patch, a thermal therapy patch, or the like.

Further, the housing 10 includes a base 11 and a cover 12 detachably attached to the base 11. Specifically, the base 11 includes an inner wall 112 and an outer wall 114 to configure the cavity 15 therebetween to store adhesive tape AT. The cover 12 is provided to cover 12 the cavity 15 in an axial direction. The cover 12 is detachably connected to the base 11 to enable the refilling of the adhesive tape AT in the cavity 15. Specifically, the cover 12 includes an internal wall 122 and an external wall 124 adapted to align correspondingly over the inner wall 112 and the outer wall 114 of the base 11 to enclose the cavity 15 to store the adhesive tape AT therein. Specifically, the cover 12 includes a top wall 123 to separate the internal wall 122 and the external wall 124 spaced at a radial distance. In the present embodiment, the internal wall 122 and the external wall 124 have a circular shape. The external wall 124 has a larger diameter than the internal wall 122.

The outer wall 114 of the base 11 and the external wall 124 of the base 11 include an outwardly extending portion configuring an outlet port 16 to dispense the adhesive tape AT therefrom. The outlet port 16 is an opening to dispense the adhesive tape AT. Specifically, while refilling the roll of adhesive tape AT, a free end of the adhesive tape AT is pulled out of the outlet port 16 before the cover 12 is attached to the base 11. Upon attaching the cover 12, the adhesive tape AT is adapted to pull out according to the user's requirement, thereby avoiding misplacement or contamination of the adhesive tape AT.

In an alternative embodiment, the cavity 15 is adapted to store adhesive patches individually, rather than the roll of adhesive tape AT.

Figure 7:
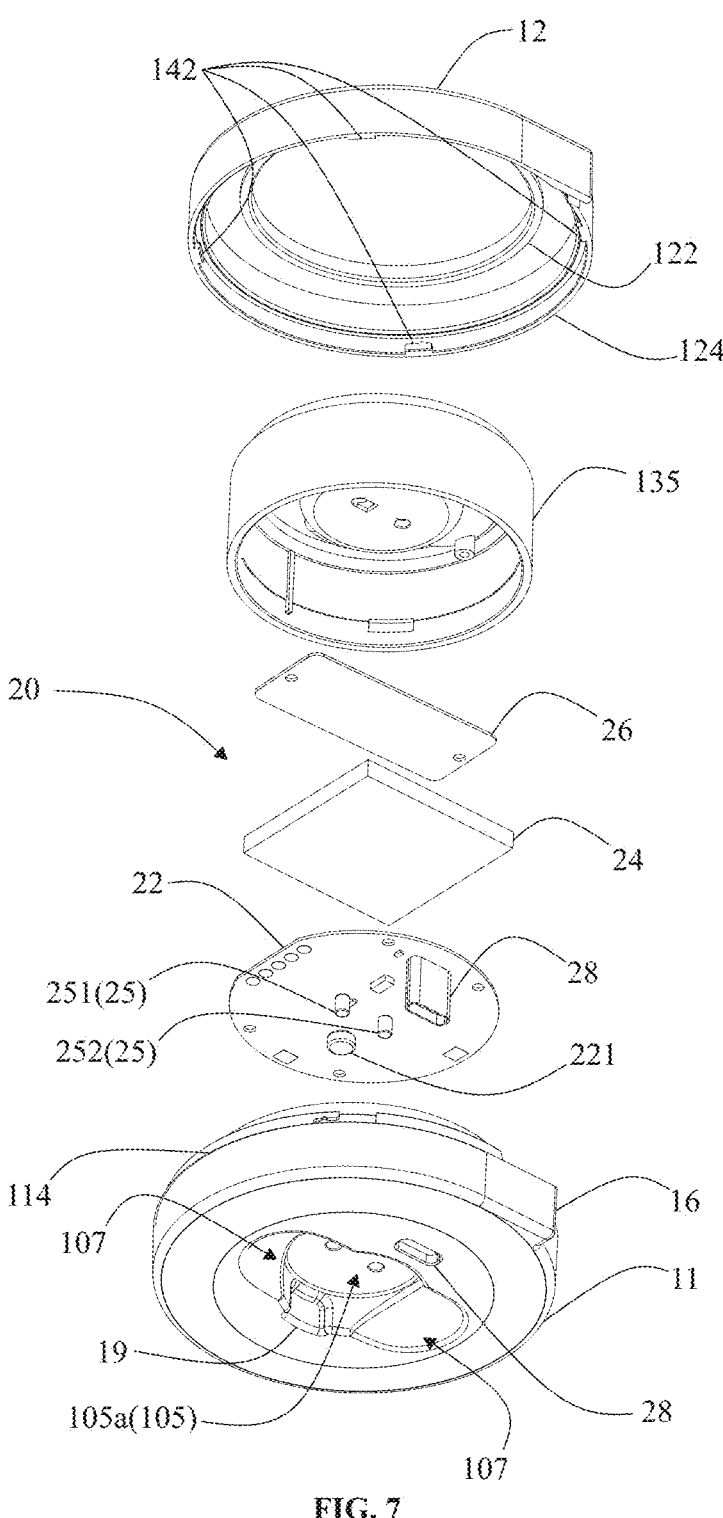
FIG. 7 shows an exploded view of the charging in accordance with the embodiment shown in FIG. 6a and FIG. 6b.
Figure 8:
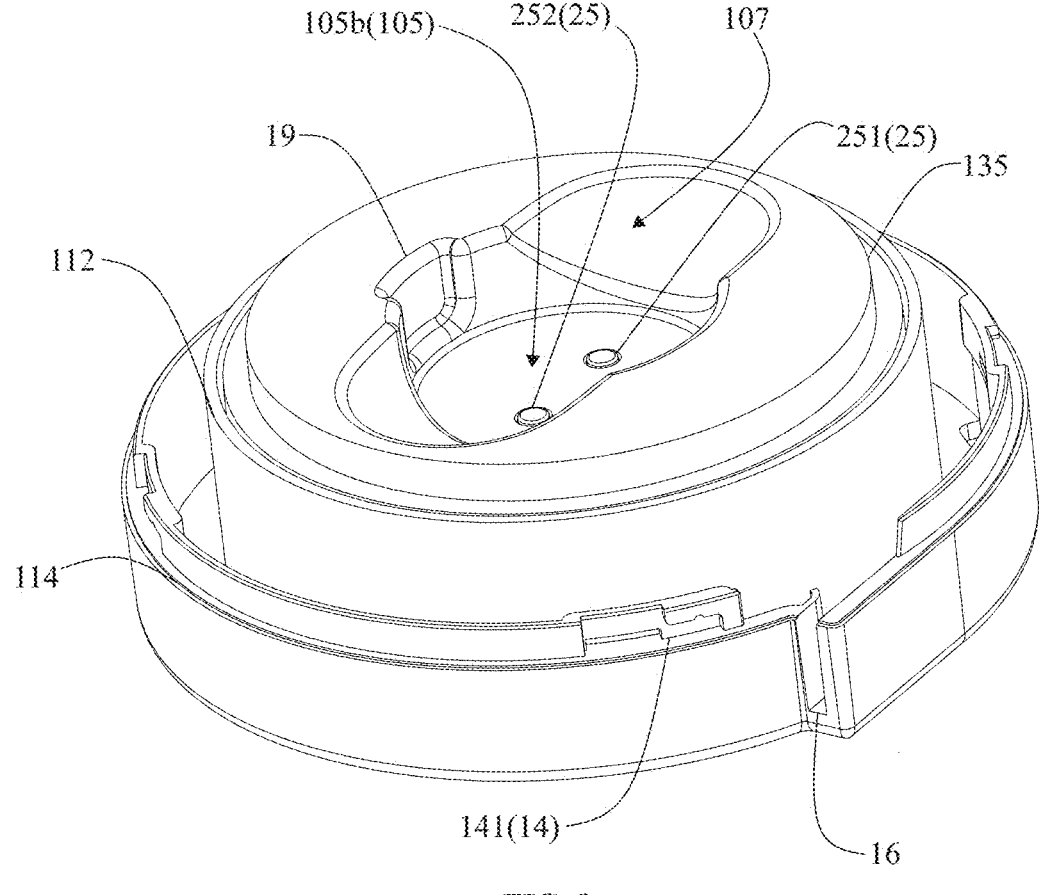

Referring now to FIGS. 7, and 8, the housing 10 is adapted to store the charging unit 20 which is configured to connect with at least one phototherapy patch 5. Specifically, the inner wall 112 of the base 11 configures a central cavity 13 shown in FIG. 3 at a central portion of the housing 10 to store the charging unit 20 therein. In the present embodiment, the housing 10 includes a central cover 135 to enclose the central cavity 13. The central cover 135 is adapted to engage with the base 11, especially, with the inner wall 112 of the base 11. The central cover 135 encloses the central cavity 13 with the charging unit 20 stored therein.

Further, the housing 10 is adapted to receive at least one phototherapy patch 5 to hold and charge the phototherapy patch 5 using the charging unit 20. The charging unit 20 is configured to connect and supply an electric charge to the phototherapy patch 5 while the phototherapy patch 5 is not being used and is attached to the housing 10.

Specifically, the housing 10 includes at least one receiving portion 105 which is adapted to receive and hold at least one phototherapy patch 5. The receiving portion 105 is a depressed region on the housing 10 having a shape corresponding to the phototherapy patch 5 to allow the phototherapy patch 5 to fit completely flush within the housing 10. In the present embodiment, the receiving portion 105 has a circular shape. It may be obvious for a person skilled in the art to configure the receiving portion 105 in any other shape, according to the shape of the phototherapy patch 5.

The receiving portion 105 is arranged corresponding to the charging unit 20 to charge the phototherapy patch 5 when attached to the housing 10. The receiving portion 105 is arranged in such a way that the charging unit 20 is exposed from the receiving portion 105 to connect with the phototherapy patch 5 to charge the phototherapy patch 5.

Further, the housing 10 includes a recessed portion 107 to allow the user to hold the phototherapy patch 5 that is attached to the housing 10. The recessed portion 107 is a depression on the housing 10 to form a space to insert fingers around the phototherapy patch 5 to facilitate holding and detachment of the phototherapy patch 5 from the housing 10. Preferably, the recessed portion 107 is configured around the receiving portion 105 and is an integral part of the receiving portion 105. The recessed portion 107 is depressed in the axial direction to expose a portion of the phototherapy patch 5 for gripping the phototherapy patch 5.

In the present embodiment, the housing 10 includes a first receiving portion 105a and a second receiving portion 105b to receive a first phototherapy patch 5a and a second phototherapy patch 5b respectively. The first receiving portion 105a is arranged on one side of the housing 10 and the second receiving portion 105b is arranged on another side of the housing 10 opposite to the first receiving portion 105a.

In an embodiment, the central cover 135 includes at least one receiving portion 105 to receive at least one phototherapy patch 5. In the preferred embodiment, the housing 10 includes a first receiving portion 105a to receive the first phototherapy patch 5a and the central cover 135 includes a second receiving portion 105b to receive the second phototherapy patch 5b.

Referring now to FIGS. 6b and 7, the charging unit 20 includes a circuit board 22, and a battery 24 connected to the circuit board 22. Further, the charging unit 20 includes a charging port 28 and a charging connector 25 arranged on the circuit board 22. The charging port 28 is configured to be exposed from the housing 10 to receive an external power to charge the battery 24. Specifically, the charging port 28 is configured outside at least one receiving portion 105 to receive the external power even if the phototherapy patch 5 is attached to the housing 10.

Further, the charging unit 20 is configured to expose the charging connector 25 from the receiving portion 105 to charge the phototherapy patch 5 attached to the receiving portion 105. Specifically, the charging connector 25 includes a first connector 251 and a second connector 252 exposed from the receiving portion 105 to connect with the phototherapy patch 5. In the preferred embodiment, the charging unit 20 includes two charging connectors, one charging connector is exposed from the first receiving portion 105a and the second charging connector is exposed from the second receiving portion 105b.

Furthermore, the charging unit 20 includes a mounting plate 26, and the circuit board 22 is mounted at the bottom of the central cavity 13, that is, at one end of the central cavity 13 away from the central cover 135. The mounting plate 26 is arranged at the top of the central cavity 13, and the battery 24 is positioned between the mounting plate 26 and the circuit board 22. The charging unit 20 includes two charging connectors, a first charging connector is arranged on the circuit board 22 corresponding to the first receiving portion 105a, and a second charging connector is arranged on the mounting plate 26 corresponding to the second receiving portion 105b and is electrically connected to the circuit board 22. The first charging connector is exposed from the first receiving portion 105a to charge the first phototherapy patch 5a. The second charging connector is exposed from the second receiving portion 105b to charge the second phototherapy patch 5b.

Figure 9:
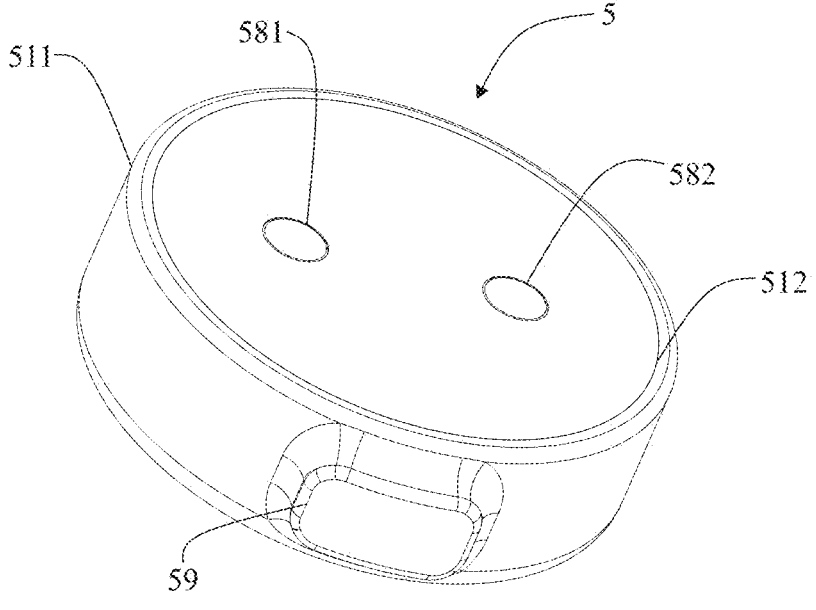
Figure 10:
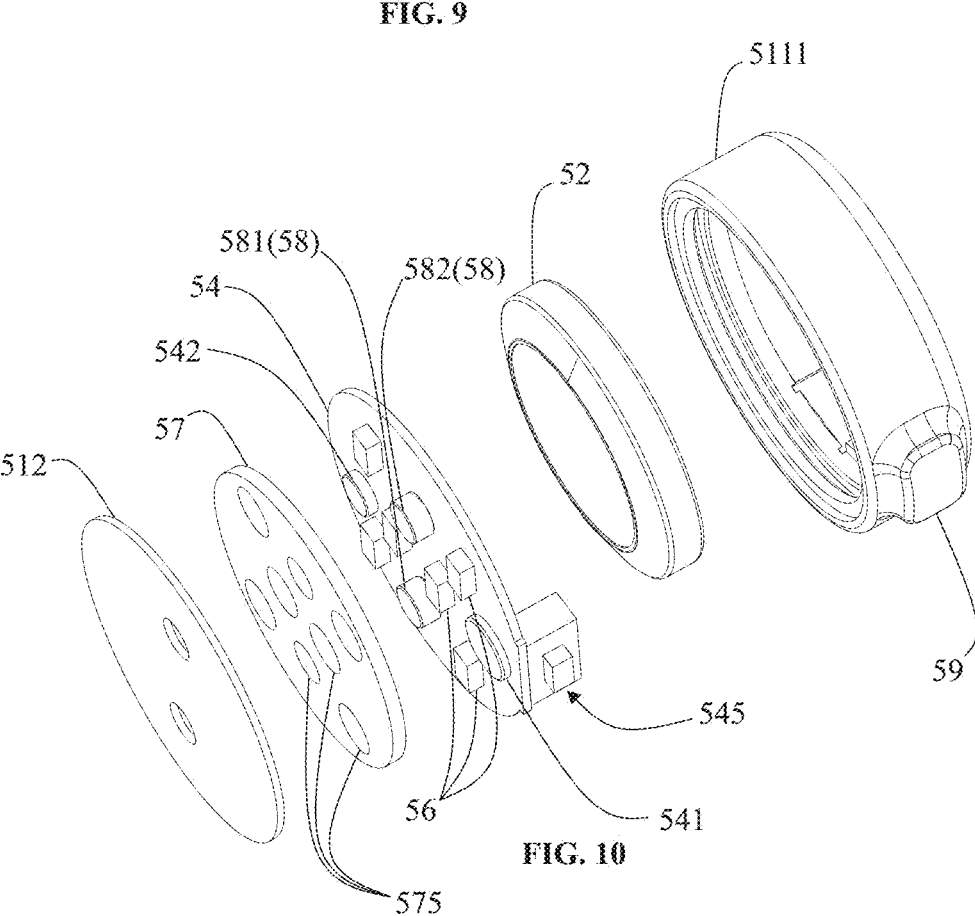
FIG. 10 shows an exploded view of the phototherapy patch illustrated in FIG. 9 in accordance with the second embodiment of the present invention.

Referring now to FIGS. 9, and 10, the phototherapy patch 5 includes a patch housing 51 adapted to accommodate a patch battery 52 and a patch circuit board 54. In the present embodiment, the phototherapy patch 5 is having a circular shape corresponding to the shape of the receiving portion 105. It may be obvious for a person skilled in the art to configure the phototherapy patch 5 in any another shape according to the shape of the receiving portion 105 of the housing 10.

The patch housing 51 includes a shell 511 and a transparent plate 512. The shell 511 is having a sidewall 5111 to configure a space to accommodate the patch battery 52 and the patch circuit board 54. The transparent plate 512 is provided to enclose the patch battery 52, and the patch circuit board 54 within the patch housing 51. The patch battery 52 is arranged in the shell 511 and the patch circuit board 54 is arranged over the patch battery 52. Specifically, the patch battery 52 and the patch circuit board 54 are having a shape corresponding to the shape of the shell 511.

Further, the patch circuit board 54 includes a light source 56 for phototherapy treatment and a charge receiving connector 58 to receive electric charge from the charging unit 20 when attached to the housing 10. The light source 56 includes a plurality of LEDs facing outward towards the transparent plate 512. The transparent plate 512 facilitates the light emission from the light source 56 on the skin of the user. The LEDs of the light source 56 are configured to emit the light in one or more of red light, infrared light, blue light, or the like.

The charge receiving connector 58 includes a third connector 581 and a fourth connector 582. The third connector 581 and the fourth connector 582 are passed through the transparent plate 512 to make contact with the first connector 251 and the second connector 252 of the charging connector 25 of the charging unit 20, when the phototherapy patch 5 is attached to the housing 10.

Specifically, the third connector 581 is provided to connect with the first connector 251 and the fourth connector 582 is provided to connect with the second connector 252. The first connector 251 and the second connector 252 are adapted to supply the electric charge to the third connector 581 and the fourth connector 582 to charge the phototherapy patch 5.

Further, the phototherapy patch 5 includes an aligning protrusion 59 arranged on the sidewall 5111 of the shell 511. The aligning protrusion 59 is provided to align the phototherapy patch 5 in the receiving portion 105 in such a way that the third connector 581 aligns with the first connector 251 and the fourth connector 582 aligns with the second connector 252 when the phototherapy patch 5 is attached to the housing 10.

Specifically, the housing 10 includes an aligning slot 19 arranged adjacent to the receiving portion 105. The aligning slot 19 is configured to receive the aligning protrusion 59 of the phototherapy patch 5 to receive and attach the phototherapy patch 5 in the required position for charging. The aligning protrusion 59 and the aligning slot 19 restrict the rotation of the phototherapy patch 5 in the receiving portion 105 to prevent connector reverse attachment, thereby ensuring the safety of the patch circuit board 54.

In an embodiment, the phototherapy patch 5 is attached to the housing 10 using a magnetic attachment to maintain the stability of the phototherapy patch 5 within the receiving portion 105 to prevent unstable contact between the charging connector 25 of the charging unit 20 and the charge receiving connector 58 of the phototherapy patch 5. At least one phototherapy patch 5 includes a first magnetic element 541 and the housing 10 includes a second magnetic element 221 to attach at least one phototherapy patch 5 to the housing 10.

Additionally, the phototherapy patch 5 includes a sensor 542 arranged on the patch circuit board 54 to detect the attachment with the housing 10. Specifically, the sensor 542 is a hall sensor adapted to detect the second magnetic element 221 of the housing 10. Upon detecting the second magnetic element 221, the phototherapy patch 5 allows the electric charge to be received from the charging unit 20.

Referring again to FIG. 10, the patch circuit board 54 includes a switch 545 arranged at a position corresponding to the aligning slot 19. The switch 545 is provided to turn ON or OFF the phototherapy patch 5 to start or stop the phototherapy treatment. The switch 545 is enclosed in the shell 511 within the aligning protrusion 59 which facilitates a pressing area for pressing the switch 545. The switch 545 is positioned corresponding to the aligning protrusion 59 to enable the user to locate the switch 545 easily.

Additionally, the phototherapy patch 5 includes a light shielding plate 57 arranged between the patch circuit board 54 and the transparent plate 512. The light shielding plate 57 includes light output holes 575 corresponding to the position of the LEDs. The light shielding plate 57 facilitates the hiding of the patch circuit board 54 to improve the appearance of the phototherapy patch 5. In another embodiment, the light shielding plate 57 may be a reflective plate, which is provided to reduce light leakage and improve light utilisation.

By way of a non-limiting example, the use of the phototherapy unit 1000 and the charging device 100 is explained. The housing 10 is provided with the cavity 15 for storing the adhesive tape AT preferably roll of adhesive tape AT. The charging unit 20 is arranged at the centre of the housing 10 to charge the phototherapy patch 5 when received within the receiving portion 105.

The phototherapy patch 5 can be removed from the charging unit 20 for individual use, and when not in use, the phototherapy patch 5 can be placed on the charging unit 20 for charging, making it easier to use again. The charging unit 20 is adapted to charge the phototherapy patch 5 when the phototherapy patch 5 is attached to the housing 10. Further, the adhesive tape AT can be used to stick the phototherapy patch 5 to the skin. Specifically, the adhesive tape AT is pulled out from the outlet port 16 and is stuck to the phototherapy patch 5. The adhesive tape AT has a first surface attachable to the phototherapy patch 5 and a second surface attachable to the skin of the user. The adhesive tape AT has an adhesion property that sticks the phototherapy patch 5 to the skin and maintains its stability during phototherapy treatment. The adhesive tape AT is made of transparent material or may have a perforated structure to allow the light to pass therethrough on the skin.

At the end of the phototherapy treatment, the adhesive tape AT can be peeled off from the skin and the phototherapy patch 5. The phototherapy patch 5 is attached to the housing 10 again. The charging device 100 and the phototherapy unit 1000 are provided for portability and facilitate the user to receive the phototherapy treatment according to the user's comfort.

Therefore, the present invention has the advantage of providing a charging device 100 for a phototherapy patch 5. The charging device 100 integrates the cavity 15 to store and dispense the adhesive tape AT to provide a portable device that secures at least one phototherapy patch 5 and charges its battery while not being used. The housing 10 of the charging device 100 is adapted to receive any type of phototherapy patch 5 and provide the electric charge when attached to the housing 10, simultaneously, the charging device 100 is adapted to store the adhesive patch, allowing the user to conveniently use adhesive patches for attaching the phototherapy patch 5 to the skin without facing problems like contamination of the adhesive patch or misplacement of adhesive patches.

The foregoing descriptions of specific embodiments of the present invention have been presented for purposes of illustration and description. They are not intended to be exhaustive or to limit the present invention to the precise forms disclosed, and obviously, many modifications and variations are possible in light of the above teaching. The embodiments were chosen and described in order to explain the principles of the present invention best and its practical application, thereby enabling others skilled in the art to best utilize the present invention and various embodiments with various modifications as are suited to the particular use contemplated. It is understood that various omission and substitutions of equivalents are contemplated as circumstance may suggest or render expedient, but such are intended to cover the application or implementation without departing from the scope of the claims of the present invention.

We claim:

1. A charging device for a phototherapy patch comprising:

a housing;

a charging unit arranged in the housing and adapted to receive and connect with at least one phototherapy patch for charging; and a cavity configured circumferentially around the charging unit for storing adhesive tape, allowing a user to use adhesive tape for attaching the phototherapy patch to the skin without misplacement of the adhesive patch, wherein the housing includes a base and a cover detachably attached to the base, wherein the cover includes an internal wall and an external wall adapted to align correspondingly over the inner wall and the outer wall of the base to enclose the cavity, wherein the outer wall of the base and the external wall of the base includes an outwardly extending portion configuring an outlet port to dispense the adhesive tape therefrom.

2. The charging device as claimed in claim 1, wherein the cavity is an annular cavity arranged around the charging unit, the annular cavity is adapted to store and dispense a roll of adhesive tape through an outlet port.

3. The charging device as claimed in claim 1, wherein the housing includes a base and a cover detachably attached to the base to refill an adhesive tape in the cavity.

4. The charging device as claimed in claim 3, wherein the base includes an inner wall and an outer wall, the inner wall and the outer wall configures the cavity therebetween, enclosed using the cover attachable to the base to store an adhesive tape therein.

5. The charging device as claimed in claim 4, wherein the inner wall of the base forms a central cavity at a central portion of the housing to accommodate a charging unit, wherein the charging unit is enclosed in the central cavity using a central cover.

6. The charging device as claimed in claim 4, wherein the cover includes an internal wall and an external wall adapted to align correspondingly over the inner wall and the outer wall of the base to enclose the cavity to store the adhesive tape therein.

7. The charging device as claimed in claim 3, wherein the cover is attachable to the base through a locking mechanism, the locking mechanism includes a first locking element and a second locking element, the first locking element is arranged on the base and the second locking element is arranged on the cover, engageable with the corresponding first locking element.

8. The charging device as claimed in claim 1, wherein the housing is adapted to receive at least one phototherapy patch in a receiving portion, wherein the phototherapy patch includes a charge receiving connector configured to engage with the charging unit to receive an electrical charge.

\* \* \* \* \*